(12) United States Patent
Fournier-Bidoz et al.

(10) Patent No.: US 8,551,763 B2
(45) Date of Patent: Oct. 8, 2013

(54) FLOW FOCUSING METHOD AND SYSTEM FOR FORMING CONCENTRATED VOLUMES OF MICROBEADS, AND MICROBEADS FORMED FURTHER THERETO

(75) Inventors: Sebastien Fournier-Bidoz, Toronto (CA); Warren Che Wor Chan, Toronto (CA)

(73) Assignee: FIO Corporation, Toronto, Ontario (CA)

( * ) Notice: Subject to any disclaimer, the term of this patent is extended or adjusted under 35 U.S.C. 154(b) by 43 days.

(21) Appl. No.: 12/682,710

(22) PCT Filed: Oct. 10, 2008

(86) PCT No.: PCT/CA2008/001808
§ 371 (c)(1),
(2), (4) Date: Dec. 13, 2010

(87) PCT Pub. No.: WO2009/046540
PCT Pub. Date: Apr. 16, 2009

(65) Prior Publication Data
US 2011/0081643 A1  Apr. 7, 2011

Related U.S. Application Data

(60) Provisional application No. 60/979,667, filed on Oct. 12, 2007.

(51) Int. Cl.
*B01J 13/08* (2006.01)
*B01F 13/08* (2006.01)
*C12M 1/02* (2006.01)
*G01N 33/545* (2006.01)

(52) U.S. Cl.
USPC ............ 435/286.5; 435/286.7; 435/5; 264/8; 264/9; 264/11

(58) Field of Classification Search
None
See application file for complete search history.

(56) References Cited

U.S. PATENT DOCUMENTS

| 5,244,630 | A | 9/1993 | Khalil et al. |
| 5,662,824 | A | 9/1997 | Sang et al. |

(Continued)

FOREIGN PATENT DOCUMENTS

| CA | 2061574 | 8/1992 |
| CA | 2021587 | 4/2003 |

(Continued)

OTHER PUBLICATIONS

Ganan-Calvo et al. Straightforward production of encoded microbeads by flow focusing: potential applications for biomolecule detection. International Journal of Pharmaceutics 2006, vol. 324, pp. 19-26.*

(Continued)

*Primary Examiner* — Shafiqul Haq
(74) *Attorney, Agent, or Firm* — Jennifer E. Lacroix, Esq.; DLA Piper LLP US (57) ABSTRACT

In a method and system for forming concentrated volumes of microbeads, a polymer solution and/or suspension includes a polymer dissolved and/or dispersed in a medium. Streams of a focusing fluid and of the polymer solution and/or suspension flow towards a fluid bath, and into intersection with one another, so &s to focus the polymer solution and/or suspension. The polymer solution and/or suspension stream forms microbeads in the fluid bath. Some of the focusing fluid is drawn from the fluid bath, so as to concentrate the microbeads in die fluid bath. The system includes a flow focusing apparatus and a liquid-containing cell. The focusing apparatus includes polymer and focusing nozzles. The cell contains the fluid bath and has an outlet port, through which the focusing fluid is drawn from the fluid bath.

32 Claims, 5 Drawing Sheets

(56) References Cited

U.S. PATENT DOCUMENTS

| | | |
|---|---|---|
| 5,714,390 A | 2/1998 | Hallowitz et al. |
| 5,786,219 A | 7/1998 | Zhang et al. |
| 5,817,458 A | 10/1998 | King et al. |
| 5,837,442 A | 11/1998 | Tsang |
| 6,011,252 A | 1/2000 | Jensen |
| 6,022,500 A | 2/2000 | John et al. |
| 6,066,243 A | 5/2000 | Anderson et al. |
| 6,100,541 A | 8/2000 | Nagle et al. |
| 6,103,379 A | 8/2000 | Margel et al. |
| 6,114,038 A | 9/2000 | Castro et al. |
| 6,116,516 A * | 9/2000 | Ganan-Calvo ............... 239/8 |
| 6,119,953 A | 9/2000 | Ganan-Calvo et al. |
| 6,172,193 B1 | 1/2001 | Primi et al. |
| 6,174,469 B1 | 1/2001 | Ganan-Calvo |
| 6,261,779 B1 | 7/2001 | Barbera-Guillem et al. |
| 6,274,323 B1 | 8/2001 | Bruchez et al. |
| 6,309,701 B1 | 10/2001 | Barbera-Guillem |
| 6,316,781 B1 | 11/2001 | Nagle et al. |
| 6,319,607 B1 | 11/2001 | Barbera-Guillem et al. |
| 6,333,110 B1 | 12/2001 | Barbera-Guillem |
| 6,340,588 B1 | 1/2002 | Nova et al. |
| 6,353,475 B1 | 3/2002 | Jensen et al. |
| 6,357,670 B2 | 3/2002 | Ganan-Calvo |
| 6,399,952 B1 | 6/2002 | Maher et al. |
| 6,409,900 B1 | 6/2002 | Parce et al. |
| 6,413,401 B1 | 7/2002 | Chow et al. |
| 6,430,512 B1 | 8/2002 | Gallagher |
| 6,468,808 B1 | 10/2002 | Nie et al. |
| 6,494,830 B1 | 12/2002 | Wessel |
| 6,498,353 B2 | 12/2002 | Nagle et al. |
| 6,504,607 B2 | 1/2003 | Jensen et al. |
| 6,506,609 B1 | 1/2003 | Wada et al. |
| 6,514,399 B1 | 2/2003 | Parce et al. |
| 6,524,793 B1 | 2/2003 | Chandler et al. |
| 6,528,165 B2 | 3/2003 | Chandler |
| 6,544,732 B1 | 4/2003 | Chee et al. |
| 6,548,171 B1 | 4/2003 | Barbera-Guillem et al. |
| 6,548,264 B1 | 4/2003 | Tan et al. |
| 6,554,202 B2 | 4/2003 | Ganan-Calvo |
| 6,576,155 B1 | 6/2003 | Barbera-Guillem |
| 6,592,821 B1 | 7/2003 | Wada et al. |
| 6,592,822 B1 | 7/2003 | Chandler |
| 6,630,307 B2 | 10/2003 | Bruchez et al. |
| 6,632,655 B1 | 10/2003 | Mehta et al. |
| 6,649,138 B2 | 11/2003 | Adams et al. |
| 6,673,662 B2 | 1/2004 | Singh |
| 6,680,211 B2 | 1/2004 | Barbera-Guillem et al. |
| 6,699,723 B1 | 3/2004 | Weiss et al. |
| 6,720,411 B2 | 4/2004 | Mirkin et al. |
| 6,734,420 B2 | 5/2004 | Empedocles et al. |
| 6,740,491 B2 | 5/2004 | Mirkin et al. |
| 6,752,966 B1 | 6/2004 | Chazan |
| 6,759,235 B2 | 7/2004 | Empedocles et al. |
| 6,767,706 B2 | 7/2004 | Quake et al. |
| 6,772,070 B2 | 8/2004 | Gilmanshin et al. |
| 6,773,812 B2 | 8/2004 | Chandler et al. |
| 6,778,724 B2 | 8/2004 | Wang et al. |
| 6,787,088 B2 | 9/2004 | Parce et al. |
| 6,835,326 B2 | 12/2004 | Barbera-Guillem |
| 6,872,249 B2 | 3/2005 | Peng et al. |
| 6,881,537 B1 | 4/2005 | Goudsmit et al. |
| 6,881,821 B2 | 4/2005 | Simmonds et al. |
| 6,890,764 B2 | 5/2005 | Chee et al. |
| 6,905,885 B2 | 6/2005 | Colston et al. |
| 6,966,880 B2 | 11/2005 | Boecker et al. |
| 6,978,212 B1 | 12/2005 | Sunshine |
| 6,986,837 B2 | 1/2006 | Chow et al. |
| 7,037,729 B2 | 5/2006 | Nie et al. |
| 7,041,362 B2 | 5/2006 | Barbera-Guillem |
| 7,069,191 B1 | 6/2006 | Moore |
| 7,077,328 B2 | 7/2006 | Kirchnaswamy et al. |
| 7,079,241 B2 | 7/2006 | Empedocles et al. |
| 7,166,475 B2 | 1/2007 | Colyer et al. |
| 7,171,983 B2 | 2/2007 | Chien et al. |
| 7,192,785 B2 | 3/2007 | Nie et al. |
| 7,243,670 B2 | 7/2007 | Witt et al. |
| 7,252,928 B1 | 8/2007 | Hafeman et al. |
| 7,267,799 B1 | 9/2007 | Borich et al. |
| 7,332,111 B2 * | 2/2008 | Grothe et al. ............... 264/11 |
| 2001/0027918 A1 | 10/2001 | Parce et al. |
| 2001/0028055 A1 | 10/2001 | Fafard et al. |
| 2001/0046602 A1 | 11/2001 | Chandler et al. |
| 2001/0055764 A1 | 12/2001 | Empedocles et al. |
| 2002/0009728 A1 | 1/2002 | Bittner et al. |
| 2002/0022273 A1 | 2/2002 | Empedocles et al. |
| 2002/0031783 A1 | 3/2002 | Empedocles et al. |
| 2002/0037499 A1 | 3/2002 | Quake et al. |
| 2002/0045045 A1 | 4/2002 | Adams et al. |
| 2002/0048425 A1 | 4/2002 | McBride et al. |
| 2002/0051971 A1 | 5/2002 | Stuelpnagel et al. |
| 2002/0059030 A1 | 5/2002 | Otworth et al. |
| 2002/0066401 A1 | 6/2002 | Peng et al. |
| 2002/0118355 A1 | 8/2002 | Worthington et al. |
| 2002/0144644 A1 | 10/2002 | Zehnder et al. |
| 2002/0164271 A1 | 11/2002 | Ho |
| 2002/0182609 A1 | 12/2002 | Arcot |
| 2003/0003441 A1 | 1/2003 | Colston et al. |
| 2003/0017264 A1 | 1/2003 | Treadway et al. |
| 2003/0026740 A1 | 2/2003 | Staats |
| 2003/0073086 A1 | 4/2003 | Guire et al. |
| 2003/0099940 A1 | 5/2003 | Empedocles et al. |
| 2003/0132538 A1 | 7/2003 | Chandler |
| 2003/0148530 A1 | 8/2003 | Lauks |
| 2003/0148544 A1 | 8/2003 | Nie et al. |
| 2003/0157327 A1 | 8/2003 | Barbera-Guillem et al. |
| 2003/0165951 A1 | 9/2003 | Bruchez, Jr. et al. |
| 2003/0170613 A1 | 9/2003 | Straus et al. |
| 2003/0172043 A1 | 9/2003 | Guyon et al. |
| 2003/0172343 A1 | 9/2003 | Leymaster et al. |
| 2003/0176183 A1 | 9/2003 | Drucker et al. |
| 2003/0177038 A1 | 9/2003 | Rao |
| 2003/0177941 A1 | 9/2003 | Barbera-Guillem |
| 2003/0190628 A1 | 10/2003 | Nakao et al. |
| 2003/0194350 A1 | 10/2003 | Stamatelos et al. |
| 2004/0009341 A1 | 1/2004 | Naasani |
| 2004/0067485 A1 | 4/2004 | Mayes et al. |
| 2004/0072428 A1 | 4/2004 | Sato et al. |
| 2004/0096363 A1 | 5/2004 | Porter |
| 2004/0101621 A1 | 5/2004 | Adams et al. |
| 2004/0106218 A1 | 6/2004 | Wang et al. |
| 2004/0118684 A1 | 6/2004 | Wainright et al. |
| 2004/0147031 A1 | 7/2004 | Nakao |
| 2004/0176704 A1 | 9/2004 | Stevens et al. |
| 2004/0203170 A1 | 10/2004 | Barbera-Guillem |
| 2004/0204633 A1 | 10/2004 | Rentea et al. |
| 2004/0229261 A1 | 11/2004 | Young |
| 2004/0241424 A1 | 12/2004 | Barbera-Guillem |
| 2004/0241752 A1 | 12/2004 | Anderson et al. |
| 2004/0247861 A1 | 12/2004 | Naasani |
| 2004/0248167 A1 | 12/2004 | Quake et al. |
| 2004/0266022 A1 | 12/2004 | Sundararajan et al. |
| 2004/0267568 A1 | 12/2004 | Chandler et al. |
| 2005/0004346 A1 | 1/2005 | Dziegiel et al. |
| 2005/0009002 A1 | 1/2005 | Chen et al. |
| 2005/0011764 A1 | 1/2005 | Berndt et al. |
| 2005/0014134 A1 | 1/2005 | West et al. |
| 2005/0032047 A1 | 2/2005 | Simmonds et al. |
| 2005/0043894 A1 | 2/2005 | Fernandez |
| 2005/0059030 A1 | 3/2005 | Bao et al. |
| 2005/0071199 A1 | 3/2005 | Riff |
| 2005/0106257 A1 | 5/2005 | Albayrak |
| 2005/0112277 A1 | 5/2005 | Banerjee et al. |
| 2005/0120946 A1 | 6/2005 | Hines et al. |
| 2005/0128479 A1 | 6/2005 | Gilbert et al. |
| 2005/0164264 A1 | 7/2005 | Shipwash |
| 2005/0214536 A1 | 9/2005 | Schrier et al. |
| 2005/0221296 A1 | 10/2005 | Simmonds et al. |
| 2005/0227370 A1 | 10/2005 | Ramel et al. |
| 2005/0239118 A1 | 10/2005 | Goudsmit et al. |
| 2006/0008921 A1 | 1/2006 | Daniels et al. |
| 2006/0012784 A1 | 1/2006 | Ulmer |
| 2006/0014040 A1 | 1/2006 | Peng et al. |
| 2006/0019098 A1 | 1/2006 | Chan et al. |
| 2006/0029267 A1 | 2/2006 | Frost et al. |

| | | | |
|---|---|---|---|
| 2006/0046330 | A1 | 3/2006 | Chen et al. |
| 2006/0063160 | A1 | 3/2006 | West et al. |
| 2006/0068203 | A1 | 3/2006 | Ying et al. |
| 2006/0078490 | A1 | 4/2006 | Shih et al. |
| 2006/0105335 | A1 | 5/2006 | Daehne et al. |
| 2006/0152372 | A1 | 7/2006 | Stout |
| 2006/0169800 | A1 | 8/2006 | Rosell |
| 2006/0173715 | A1 | 8/2006 | Wang |
| 2006/0194030 | A1 | 8/2006 | Barbera-Guillem |
| 2007/0020779 | A1 | 1/2007 | Stavis et al. |
| 2007/0031283 | A1 | 2/2007 | Davis et al. |
| 2007/0081920 | A1 | 4/2007 | Murphy et al. |

FOREIGN PATENT DOCUMENTS

| | | |
|---|---|---|
| CA | 2518352 | 3/2005 |
| EP | 1315099 | 5/2003 |
| JP | 2002-271 | 1/2002 |
| JP | 2005-508493 | 3/2005 |
| WO | 99/19000 | 4/1999 |
| WO | 99/36564 | 7/1999 |
| WO | 99/64840 | 12/1999 |
| WO | 99/66318 | 12/1999 |
| WO | 00/13580 | 3/2000 |
| WO | 00/28598 | 5/2000 |
| WO | 00/70080 | 11/2000 |
| WO | 01/20533 | 3/2001 |
| WO | 01/89585 | 11/2001 |
| WO | 01/93754 | 12/2001 |
| WO | 02/04484 | 1/2002 |
| WO | 03/003015 | 1/2003 |
| WO | 2004/008550 | 1/2004 |
| WO | 2004/040319 | 5/2004 |
| WO | 2005/023923 | 3/2005 |
| WO | 2005/031802 | 4/2005 |
| WO | 2005/052996 | 6/2005 |
| WO | 2005/053649 | 6/2005 |
| WO | 2005/061095 | 7/2005 |
| WO | 2006/033732 | 3/2006 |
| WO | 2006/045004 | 4/2006 |
| WO | 2006/072306 | 7/2006 |
| WO | 2006/132953 | 12/2006 |
| WO | 2007/011622 | 1/2007 |
| WO | 2008/089155 | 7/2008 |
| WO | 2008/147382 | 12/2008 |
| WO | 2009/059404 | 5/2009 |

OTHER PUBLICATIONS

Nie et al. Janus and ternary particles generated by microfluidic systhesis: design, synthesis, and self-assembly. J. Am. Chem. Soc. 2006, vol. 128, pp. 9408-9412.*
Seo et al. Microfluidic consecutive flow-focusing droplet generators. Soft Matters 2007, vol. 3, pp. 986-992.*
Alivisatos, A.P., Perspectives on the Physical Chemistry of Semiconductor Nanocrystals, Journal of Physical Chemistry, 1996, pp. 13226-13239, vol. 100, No. 31, American Chemical Society, USA.
Bakalova, Rurniana et al., Quantum dot-conjugated hybridization probes for preliminary screening of siRNA sequences, Journal of the American Chemical Society, Aug. 1, 2005, pp. 11328-11335, vol. 127, No. 32, American Chemical Society, USA.
Boldt, Klaus et al., Comparative Examination of the Stability of Semiconductor Quantum Dots in Various Biochemical Buffers, Journal of Physical Chemistry B, 2006, pp. 1959-1963, vol. 110, No. 5, American Chemical Society, USA.
Branch, Mary Ann et al., A Subspace, Interior, and Conjugate Gradient Method for Large-Scale Bound-Constrained Minimization Problems, SIAM J. Sci. Comput., Aug. 3, 1999, pp. 1-23, vol. 21, No. 1, Society for Industrial and Applied Mathematics.
Bruchez, Marcel Jr. et al., Semiconductor Nanocrystals as Fluorescent Biological Labels, Science, Sep. 25, 1998, pp. 2013-2015, vol. 281, American Association for the Advancement of Science, USA.
Burns, Mark A. et al., An Integrated Nanoliter DNA Analysis Device, Science, Oct. 16, 1998, pp. 484-487, vol. 282, No. 5388, American Association for the Advancement of Science, USA.
Chabinyc, Michael L. et al., An Integrated Fluorescence Detection System in Poly(dimethylsiloxane) for Microfluidic Applications, Analytical Chemistry, Sep. 15, 2001, pp. 4494-4498, vol. 73, No. 18, American Chemical Society, USA.
Chan, Eugene Y. et al., DNA Mapping Using Microfluidic Stretching and Single-Molecule Detection of Fluorescent Site-Specific Tags, Genome Research, 2004, pp. 1137-1146, vol. 14, Cold Spring Harbour Laboratory Press, USA.
Chan, Warren C.W. et al., Luminescent quantum dots for multiplexed biological detection and imaging, Current Opinion in Biotechnology, 2002, pp. 40-46, vol. 13, Elsevier Science Ltd.
Chan, Warren C.W. et al., Quantum Dot Bioconjugates for Ultrasensitive Nonisotopic Detection, Science, Sep. 25, 1998, pp. 2016-2018, vol. 281, American Association for the Advancement of Science, USA.
Chou, Hou-Pu et al., A microfabricated device for sizing and sorting DNA molecules, PNAS—Proceedings of the National Academy of Sciences of the United States of America, Jan. 1999, pp. 11-13, vol. 96, The National Academy of Sciences, USA.
Dabbousi, B.O. et al., (CdSe)ZnS Core-Shell Quantum Dots: Synthesis and Characterization of a Size Series of Highly Luminescent Nanocrystallites, Journal of Physical Chemistry B, 1997, pp. 9463-9475, vol. 101, No. 46, American Chemical Society, USA.
Duffy, D.C. et al., Rapid Prototyping of Microfulidic Systems in Poly(dimethylsiloxane), Analytical Chemistry, Dec. 1, 1998, pp. 4974-4984, vol. 70, No. 23, American Chemical Society, USA.
Eisenstein, Michael, Technology Feature: Protein Arrays—Growing pains, Losing the Label, an Apt Solution? & (Almost) No Assembly Required, Nature, Dec. 14, 2006, pp. 959-962, vol. 444, Nature Publishing Group, USA.
Fournier-Bidoz, Sebastien et al., Facile and Rapid One-Step Mass Preparation of Quantum-Dot Barcodes, Angewandte Chemie International Edition, 2008, pp. 5577-5581, vol. 47, No. 30, Wiley-VCH Verlag GmbH & Co. KGaA, Weinheim.
Fu, Anne Y. et al., A microfabricated fluorescence-activated cell sorter, Nature Biotechnology, Nov. 1999, pp. 1109-1111, vol. 17, Nature America Inc., USA.
Fu, Lung-Ming et al., Multiple injection techniques for microfluidic sample handling, Electrophoresis, 2003, pp. 3026-3032, vol. 24, Wiley-VCH Verlag GmbH & Co. KGaA, Weinheim.
Gao, Xiaohu et al., In vivo cancer targeting and imaging with semiconductor quantum dots, Nature Biotechnology, Jul. 18, 2004, pp. 969-976, vol. 22, No. 8, Nature Publishing Group, USA.
Gao, Xiaohu et al., Quantum Dot-Encoded Mesoporous Beads with High Brightness and Uniformity: Rapid Readout Using Flow Cytometry, Analytical Chemistry, Apr. 15, 2004, pp. 2406-2410, vol. 76, No. 8, American Chemical Society, USA.
Gao, Xiaohu et al., Quantum-dot nanocrystals for ultrasensitive biological labelling and mulitcolor optical encoding, Journal of Biomedical Optics, Oct. 2002, pp. 532-537, vol. 7, No. 4, SPIE.
Gaponik, Nikolai et al., Toward Encoding Combinatorial Libraries: Charge-Driven Microencapsulation of Semiconductor Nanocrystals Luminescing in the Visible and Near IR, Advanced Materials, Jun. 18, 2002, pp. 879-882, vol. 14, No. 12, Wiley-VCH Verlag GmbH, Weinheim.
Gershon, Diane, Technology Feature: DNA Microarrays—More than than gene expression, It's a Small World, Microassays Move Downstream & on the Hardware Front, Nature, Oct. 20, 2005, pp. 1195-1198, vol. 437, Nature Publishing Group, USA.
Goluch, E.D. et al., A bio-barcode assay for on-chip attomolar-sensitivity protein detection, Lab on a Chip, Aug. 15, 2006, pp. 1293-1299, vol. 6, The Royal Society of Chemistry.
Grumann, M. et al., Parallelization of Chip-Based Fluorescence Immuno-Assays with Quantum-Dot Labelled Beads, The 13th International Conference on Solid-State Sensors, Actuators and Microsystems, Jun. 2005, pp. 1114-1117, IEEE.
Han, Mingyong et al., Quantum-dot-tagged microbeads for multiplexed optical coding of biomolecules, Nature Biotechnology, Jul. 2001, pp. 631-635, vol. 19, Nature Publishing Group, USA.
Hines, Margaret A. et al., Synthesis and Characterization of Strongly Luminescing ZnS-Capped CdSe Nanocrystals, Journal of Physical Chemistry B, 1996, pp. 468-471, vol. 100, No. 2, American Chemical Society, USA.

Kloepfer, Jeremiah A. et al., Photophysical Properties of Biologically Compatible CdSe Quantum Dot Structures, Journal of Physical Chemistry B, 2005, pp. 9996-10003, vol. 109, No. 20, American Chemical Society, USA.

Klostranec, Jesse M. et al., Convergence of Quantum Dot Barcodes with Microfluidics and Signal Processing for Multiplexed High-Throughput Infectious Disease Diagnostics, Nano Letters, Aug. 18, 2007, pp. 2812-2818, vol. 7, No. 9, American Chemical Society, USA.

Klostranec, Jesse M. et al., Quantum Dots in Biological and Biomedical Research: Recent Progress and Present Challenges, Advanced Materials, Aug. 4, 2006, pp. 1953-1964, vol. 18, No. 15, Wiley-VCH Verlag GmbH & Co. KGaA, Weinheim.

Li, Yougen et al., Multiplexed detection of pathogen DNA with DNA-based fluorescence nanobarcodes, Nature Biotechnology, Jul. 2005, pp. 885-889, vol. 23, No. 7, Nature Publishing Group, USA.

Liu, Wen-Tso et al., Microfluidic device as a new platform for immunofluorescent detection of viruses, Lab on a Chip, Oct. 4, 2005, pp. 1327-1330, vol. 5, The Royal Society of Chemistry.

Malamud, D. et al., Point Detection of Pathogens in Oral Samples, Adv Dent Res, Jun. 2005, pp. 12-16, vol. 18.

Marti et al., Design and characterization of two-dye and three-dye binary fluorescent probes for mRNA detection, Tetrahedron, Mar. 21, 2007, pp. 3591-3600, vol. 63, No. 17, Elsevier Science Publishers, Amsterdam, NL.

Mattoussi, H. et al., Luminescent Quantum Dot-Bioconjugates in Immunoassays, FRET, Biosensing, and Imaging Applications, JALA—Journal of the Association for Laboratory Automation, Feb. 2004, pp. 28-32, vol. 9, No. 1, The Association for Laboratory Automation, USA.

Medintz, Igor L. et al., Quantum dot bioconjugates for imaging, labelling and sensing, Nature Materials, Jun. 2005, pp. 435-446, vol. 4, Nature Publishing Group, USA.

Moré, Jorge J. et al., Computing a Trust Region Step, SIAM J. Sci, Stat. Comput., Sep. 1983, pp. 553-572, vol. 4, No. 3, Society for Industrial and Applied Mathematics.

Murray, C.B. et al., Synthesis and Characterization of Nearly Monodisperse CdE (E=S, Se, Te) Semiconductor Nanocrystallites, Journal of the American Chemical Society, 1993, pp. 8706-8715, vol. 115, No. 19, American Chemical Society, USA.

Neogi, A. et al., Enhanced luminescence efficiency from hydrogel microbead encapsulated quantum dots, Materials Research Society Symposium Proceedings, Jan. 1, 2007, pp. 202-207, vol. 959, Materials Research Society, USA.

Peng, Xiaogang et al., Epitaxial Growth of Highly Luminescent CdSe/CdS Core/Shell Nanocrystals with Photostability and Electronic Accessibility, Journal of the American Chemical Society, 1997, pp. 7019-7029, vol. 119, No. 30, American Chemical Society, USA.

Pregibon, Daniel C. et al., Multifunctional Encoded Particles for High-Throughput Biomolecule Analysis, Science, Mar. 9, 2007, pp. 1393-1396, vol. 315, American Association for the Advancement of Science, USA [downloaded on Mar. 9, 2009 from http://www.sciencemag.org].

Sathe, Tushar R. et al., Mesoporous Silica Beads Embedded With Semiconductor Quantum Dots and Iron Oxide Nanocrystals: Dual-Function Microcarriers for Optical Encoding and Magnetic Separation, Analytical Chemistry, Jul. 20, 2006, pp. 5627-5632, , vol. 78, No. 16, American Chemical Society, USA.

Service, Robert F., DNA Analysis: Microchip Arrays Put DNA on the Spot, Science, Oct. 16, 1998, pp. 396-399, vol. 282, No. 5388, American Association for the Advancement of Science, USA [downloaded on Mar. 20, 2008 from http://www.science mag.org/cgi/content/full/282/5388/396].

Stavis, Samuel M. et al., Single molecule studies of quantum dot conjugates in a submicrometer fuidic channel, Lab on a Chip, Jan. 13, 2005, pp. 337-343, vol. 5, The Royal Society of Chemistry.

Sukhanova, A. et al., Nanocrystal-encoded fluorescent microbeads for proteomics: Antibody profiling and diagnostics of autoimmune diseases, Nano Letters, Aug. 2007, pp. 2322-2327, vol. 7, No. 8, American Chemical Society, USA.

Thomson, B. et al, Dispersion Copolymerization of Styrene and Divinylbenzee. II. Effect of Crosslinker on Particle Morphology, Journal of Applied Polymer Science, 1996, pp. 2009-2028, vol. 59, John Wiley & Sons, Inc.

Xu, Hongxia et al., Muliplexed SNP genotyping using the Qbead™ system: a quantum dot-encoded microsphere-based assay, Nucleic Acids Research, 2003, pp. 1-10, vol. 31, No. 8, Oxford University Press.

Xuan, Xiangchun et al., Focused electrophoretic motion and selected electrokinetic dispensing of particles of particles and cells in cross-microchannels, Electrophoresis, 2005, pp. 3552-3560, vol. 26, WILEY-VCH Verlag GmbH & Co. KGaA, Weinheim.

Yun, Kwang-Seok et al,, A microfluidic chip for measurement of biomolecules using a microbead-based quantum dot fluorescence assay, Measurement Science and Technology, 2006, pp. 3178-3183, vol. 17, IOP Publishing Ltd, UK.

Zaytseva, Natalya V. et al., Development of a microfluidic biosensor module for pathogen detection, Lab on a Chip, Jul. 6, 2005, pp. 805-811, vol. 5, The Royal Society of Chemistry.

* cited by examiner

FLOW FOCUSING METHOD AND SYSTEM FOR FORMING CONCENTRATED VOLUMES OF MICROBEADS, AND MICROBEADS FORMED FURTHER THERETO

FIELD OF THE INVENTION

The present invention relates generally to a method and system for forming microbeads, and more particularly, to a flow focusing method and system for forming concentrated volumes of microbeads, and to microbeads formed farther thereto.

BACKGROUND OF THE INVENTION

It may be preferable for large scale manufacture of microbeads (such as, for example, polymer microbeads) to allow for the control of various parameters. Some of these parameters may include, among others, control over: (i) bead diameter, (ii) degree of monodispersity, (iii) bead surface morphology and functionality, and/or (iv) rate of production—i.e., preferably, so as to enable a high-throughput.

The act of binding nanoparticles—such as quantum dots (QDs)—to polymer microbeads (e.g., for the use in diagnostic applications) may create additional manufacturing challenges and/or may increase the need for high quality, uniform and stable polymer beads. These and other potential uses for polymer microbeads may create a significant need for a large-scale method and system for forming same.

There is a known process for making polymer microbeads (or "microspheres" as they are sometimes called) which uses a flow focusing technique. Issued U.S. Pat. No. 6,116,516 (Ganan-Calvo) is illustrative in this regard. Heretofore, however, it may not have been readily apparent to those of ordinary skill in the art how one might adapt such flow focusing techniques to make polymer microbeads incorporating nanoparticles (e.g., in particular, QDs and/or magnetic nanoparticles), inter alia, in a one-step method. That is, known processes may not have been readily adaptable for use in association with the large-scale production of such polymer microbeads.

There may, therefore, exist a need for a novel method and system for large-scale manufacture of polymer microbeads.

Prior art flow focusing techniques may have been somewhat unsuitable for the manufacture of microbeads in large quantities (e.g., quantities of microbeads having a collective weight of several grams), perhaps in part because of the significant volume of 'waste' liquid used during the process. The significant amount of liquid previously used may have been due, to a great extent, on the substantial flow rate of the focusing liquid. It may be desirable to effectively address and creatively solve this problem—i.e., to deal with the large volumes of liquid previously used by flow focusing techniques for forming polymer microbeads—since it is one which may severely limit current production rates for microbeads. There may exist a need for a method and system for microbead manufacture which may minimize and/or reduce the amount of focusing fluid used, and/or which may afford greater control over the amount of focusing fluid produced.

A potentially serious concern arising from prior art microbead production methods may have been the generally low concentrations of microbeads so produced. Perhaps due in part to the volume of focusing liquid required in the prior art, microbeads may typically only be present in relatively low concentrations in product solutions (e.g., <0.02 wt %). Accordingly, for many microbead applications, additional steps (e.g., one or more centrifugations) may have been employed, on a more or less widespread basis, to bring the microbeads up to usable concentrations. In view thereof, there may exist a need for a method and system for forming, or manufacturing, microbeads at higher concentrations. Preferably, such a method or system would minimize, reduce or entirely eliminate any need to perform any additional concentrating steps.

It is, therefore, an object of one preferred embodiment according to the invention to provide a method and/or a system for forming microbeads.

It is an object of one preferred embodiment according to the invention to provide a method and/or a system for forming polymer microbeads.

It is an object of one preferred embodiment according to the invention to provide a method and/or a system for large-scale and/or high-throughput manufacture of microbeads.

It is an object of one preferred embodiment according to the invention to provide a method and/or a system for forming microbeads which affords increased control over: (i) bead diameter, (ii) degree of monodispersity, (iii) bead surface morphology and functionality, and/or (iv) rate of production.

It is an object of one preferred embodiment according to the invention to provide a method and/or a system for large-scale manufacture of microbeads binding nanoparticles, such as QDs.

It is an object of one preferred embodiment according to the invention to provide a method and/or a system for large-scale manufacture of high-quality, uniform and/or stable microbeads.

It is an object of one preferred embodiment according to the invention to provide a method and/or a system for large-scale manufacture of highly concentrated volumes of microbeads.

It is an object of one preferred embodiment according to the invention to provide a method and/or a system for large-scale manufacture of microbeads which reduces, minimizes and/or eliminates any need for subsequent centrifugation steps to concentrate same.

It is an object of one preferred embodiment according to the invention to provide a method and/or a system for large-scale flow focusing manufacture of microbeads which reduces and/or minimizes the amount of focusing fluid used, and/or which affords greater control over the amount of focusing fluid produced.

It is an object of one preferred embodiment according to the invention to provide a method and/or a system for large-scale flow focusing manufacture of microbeads, with the method and/or system being adapted to recycles at least some of the focusing fluid used.

It is an object of the present invention to obviate or mitigate one or more of the aforementioned disadvantages associated with the prior art, and/or to achieve one or more of the aforementioned objects of the invention.

SUMMARY OF THE INVENTION

According to the invention, there is disclosed a method of forming one or more concentrated volumes of microbeads. The method includes steps (a), (b), (c) and (d). In step (a) a focused stream of a polymer solution and/or suspension is flowed towards a fluid bath. The polymer solution and/or suspension includes a polymer dissolved and/or dispersed in a medium. In step (b), a focusing stream of a focusing fluid is flowed towards the fluid bath, and into intersection with the focused stream. In step (c), the focusing stream and the focused stream are flowed from intersection with one another, so as to form the microbeads in the fluid bath. In step (d), a volume of the focusing fluid is flowed from the fluid bath, so as to concentrate the microbeads in the fluid bath.

According to an aspect of one preferred embodiment of the invention, the method may preferably, but need not necessarily, also include step (b.1), preferably after step (b), of maintaining the fluid bath under stirring. The microbeads may preferably, but need not necessarily, be allowed to solidify in step (c).

According to the invention, there is also disclosed a method of forming one or more concentrated volumes of microbeads, which includes steps (a), (b), (b.1), (c) and (d). In step (a) a focused stream of a polymer solution and/or suspension is flowed towards a fluid bath. The polymer solution and/or suspension includes a polymer dissolved and/or dispersed in a medium. In step (b), a focusing stream of a focusing fluid is flowed towards the fluid bath, and into intersection with the focused stream. In step (b.1), preferably after step (b), the fluid bath is maintained under stirring. In step (c), the focusing stream and the focused stream are flowed from intersection with one another, so as to form the microbeads in the fluid bath, and the microbeads are allowed to solidify. In step (d), a volume of the focusing fluid is flowed from the fluid bath, so as to concentrate the microbeads in the fluid bath.

According to an aspect of one preferred embodiment of the invention, preferably in step (d), the fluid bath may preferably, but need not necessarily, be controlled so as to be maintained at a substantially constant liquid level.

According to an aspect of one preferred embodiment of the invention, the substantially constant liquid level may preferably, but need not necessarily, be maintained by balancing respective flow rates for the focused stream in step (a), the focusing stream in step (b), and/or the focusing fluid in step (d).

According to an aspect of one preferred embodiment of the invention, preferably in step (d), the volume of the focusing fluid may preferably, but need not necessarily, flow through one or more filters.

According to an aspect of one preferred embodiment of the invention, preferably in step (d), the filters may preferably, but need not necessarily, retain the microbeads—preferably, in the fluid bath.

According to an aspect of one preferred embodiment of the invention, preferably in step (d), the filters may preferably, but need not necessarily, retain a substantially monodisperse set of the microbeads, preferably in the fluid bath.

According to an aspect of one preferred embodiment of the invention, preferably in step (d), the filters may preferably, but need not necessarily, divide the microbeads into one or more collections of microbeads. Each of the collections may preferably, but need not necessarily, include a respectively monodisperse set of the microbeads.

According to an aspect of one preferred embodiment of the invention, preferably at least one of steps (a) and (b) may preferably, but need not necessarily, be performed within an interior chamber of a flow focusing body.

According to an aspect of one preferred embodiment of the invention, steps (a) and (b) may preferably, but need not necessarily, be both performed within the interior chamber of the flow focusing body. An outlet portion of the flow focusing body may preferably, but need not necessarily, be located below a liquid level of the fluid bath. Preferably in step (c), the focusing stream and the focused stream may preferably, but need not necessarily, flow out from the outlet portion of the flow focusing body.

According to an aspect of one preferred embodiment of the invention, preferably in step (b), the focused stream may preferably, but need not necessarily, be focused by the focusing fluid. Preferably in step (c), the focusing stream and the focused stream may preferably, but need not necessarily, flow out from the outlet portion as a single flow stream.

According to an aspect of one preferred embodiment of the invention, preferably in step (c), the focusing stream may preferably, but need not necessarily, substantially surround the focused stream—preferably, in the single flow stream.

According to an aspect of one preferred embodiment of the invention, the method may preferably, but need not necessarily, also include a preliminary step, preferably before step (a), of providing the fluid bath within a sealed liquid-containing cell.

According to an aspect of one preferred embodiment of the invention, preferably at least one of steps (a) through (c) may preferably, but need not necessarily, be performed within the liquid-containing cell.

According to an aspect of one preferred embodiment of the invention, preferably in the preliminary step, the liquid-containing cell may preferably, but need not necessarily, additionally contain a volume of a gas, preferably at a predetermined pressure.

According to an aspect of one preferred embodiment of the invention, preferably in the preliminary step, a gas pressure source may preferably, but need not necessarily, pressurize the gas, preferably via an inlet valve, and preferably in the sealed liquid-containing cell.

According to an aspect of one preferred embodiment of the invention, the method may preferably, but need not necessarily, also include step (c.1), preferably after the preliminary step, of releasing a portion of the gas or the fluid bath, preferably via a pressure safety valve, and preferably when the pressure exceeds a predetermined maximum safety pressure for the sealed liquid-containing cell.

According to an aspect of one preferred embodiment of the invention, the gas may preferably, but need not necessarily, include an inert gas.

According to an aspect of one preferred embodiment of the invention, the pressure of the gas in the preliminary step may preferably, but need not necessarily, be predetermined—preferably, in balance with respective flow rates for the focused stream in step (a) and/or the focusing stream in step (b)—to maintain the fluid bath at a substantially constant liquid level.

According to an aspect of one preferred embodiment of the invention, preferably in step (b.1), a stirring bar may preferably, but need not necessarily, maintain the fluid bath under stirring. The stirring bar may preferably, but need not necessarily, include an electric stirring bar or a magnetic stirring bar.

According to an aspect of one preferred embodiment of the invention, the method may preferably, but need not necessarily, also include step (d.1), preferably after step (d), wherein substantially solidified microbeads may preferably, but need not necessarily, be recovered from the fluid bath.

According to an aspect of one preferred embodiment of the invention, the method may preferably, but need not necessarily, also include step (e) of recycling at least part of the volume of the focusing fluid, preferably flowing from the fluid bath in step (d), and preferably as at least part of the focusing stream flowing into intersection with the focused stream in step (b).

According to the invention, there is disclosed a method of forming one or more concentrated volumes of microbeads, which includes steps (a), (b), (c), (d) and (e). In step (a) a focused stream of a polymer solution and/or suspension is flowed towards a fluid bath. The polymer solution and/or suspension includes a polymer dissolved and/or dispersed in a medium. In step (b), a focusing stream of a focusing fluid is flowed towards the fluid bath, and into intersection with the focused stream. In step (c), the focusing stream and the focused stream are flowed from intersection with one another, so as to form the microbeads in the fluid bath. In step (d), a volume of the focusing fluid is flowed from the fluid bath, so as to concentrate the microbeads in the fluid bath. In step (e), at least part of the volume of the focusing fluid, flowing from the fluid bath in step (d), is recycled as at least part of the focusing stream flowing into intersection with the focused stream in step (b).

According to an aspect of one preferred embodiment of the invention, preferably in step (a), the medium may preferably, but need not necessarily, include an organic solvent.

According to an aspect of one preferred embodiment of the invention, preferably in step (a), the polymer may preferably, but need not necessarily, be substantially hydrophobic.

According to an aspect of one preferred embodiment of the invention, preferably in step (a), the polymer may preferably, but need not necessarily, include a polystyrene powder and/or a derivative thereof.

According to an aspect of one preferred embodiment of the invention, preferably in step (b), the focusing fluid may preferably, but need not necessarily, include water.

According to an aspect of one preferred embodiment of the invention, preferably in step (a), the polymer solution and/or suspension may preferably, but need not necessarily, also include particles dissolved and/or dispersed in the medium. Preferably in step (c), each of the microbeads may preferably, but need not necessarily, bind an identifiable set of the particles.

According to an aspect of one preferred embodiment of the invention, preferably in step (a), the particles may preferably, but need not necessarily, include fluorophores.

According to an aspect of one preferred embodiment of the invention, preferably in step (a), the particles may preferably, but need not necessarily, include nanoparticles.

According to an aspect of one preferred embodiment of the invention, preferably in step (a), the particles may preferably, but need not necessarily, include quantum dots.

According to an aspect of one preferred embodiment of the invention, preferably in step (a), the particles may preferably, but need not necessarily, include a combination of quantum dots and/or magnetic nanoparticles.

According to an aspect of one preferred embodiment of the invention, preferably in step (a), the polymer solution and/or suspension may preferably, but need not necessarily, have a concentration of about 0.04 by weight-weight percentage (4 wt %).

According to the invention, there is also disclosed a microbead formed according to the method in any one of the above methods.

According to an aspect of one preferred embodiment of the invention, the microbead may preferably, but need not necessarily, include one or more functional groups at a surface thereof. The functional groups may preferably, but need not necessarily, be adapted to operatively bind with biorecognition molecules.

According to an aspect of one preferred embodiment of the invention, the microbead—preferably, operatively bound with the biorecognition molecules—may preferably, but need not necessarily, be adapted for use as a probe, preferably in a multiplexed diagnostic test, and preferably for detection of one or more diseases.

According to an aspect of one preferred embodiment of the invention, the diseases may preferably, but need not necessarily, include malaria, HIV, Hepatitis B, Hepatitis C, Dengue virus, and/or avian flu (H5N1).

According to an aspect of one preferred embodiment of the invention, the microbead—preferably, operatively bound with the biorecognition molecules—may preferably, but need not necessarily, be adapted for use as a probe, preferably in a multiplexed diagnostic test, and preferably for detection of one or more genetic expression factors.

According to the invention, there is also disclosed a concentrated volume of microbeads formed according to the method in any one of the above methods.

According to an aspect of one preferred embodiment of the invention, one or more of the microbeads in the concentrated volume may preferably, but need not necessarily, include one or more functional groups at a surface thereof. The functional groups may preferably, but need not necessarily, be adapted to operatively bind with biorecognition molecules.

According to an aspect of one preferred embodiment of the invention, one or more of the microbeads in the concentrated volume—preferably, operatively bound with the biorecognition molecules—may preferably, but need not necessarily, be adapted for use as a probe, preferably in a multiplexed diagnostic test, and preferably for detection of one or more diseases.

According to an aspect of one preferred embodiment of the invention, the diseases may preferably, but need not necessarily, include malaria, HIV, Hepatitis B, Hepatitis C, Dengue virus, and/or avian flu (H5N1).

According to an aspect of one preferred embodiment of the invention, one or more of the microbeads in the concentrated volume—preferably, operatively bound with the biorecognition molecules—may preferably, but need not necessarily, be adapted for use as a probe, preferably in a multiplexed diagnostic test, and preferably for detection of one or more genetic expression factors.

According to the invention, there is additionally disclosed a system for forming one or more concentrated volumes of microbeads. The system includes a fluid bath, a focusing fluid, and a polymer solution and/or suspension including a polymer dissolved and/or dispersed in a medium. The system also includes a flow focusing apparatus. The flow focusing apparatus includes a polymer nozzle and a focusing nozzle. The polymer nozzle operatively delivers a focused stream of the polymer solution and/or suspension. The focusing nozzle operatively delivers a focusing stream of the focusing solution. The flow focusing apparatus operatively delivers the focused stream and the focusing stream into intersection with one another. The flow focusing apparatus operatively flows the focusing stream and the focused stream into the fluid bath, so as to form the microbeads in the fluid bath. The system also includes a liquid-containing cell which is shaped to define an outlet port. The liquid-containing cell operatively contains the fluid bath. The liquid-containing cell operatively delivers a volume of the focusing fluid out from the fluid bath, via the outlet port, so as to concentrate the microbeads in the fluid bath.

According to an aspect of one preferred embodiment of the invention, the liquid-containing cell further may preferably, but need not necessarily, include a stirring bar. The stirring bar may preferably, but need not necessarily, operatively maintain the fluid bath under stirring. The fluid bath may preferably, but need not necessarily, operatively allow the microbeads to solidify.

According to the invention, there is additionally disclosed another system for forming one or more concentrated volumes of microbeads. The system includes a fluid bath, a focusing fluid, and a polymer solution and/or suspension including a polymer dissolved and/or dispersed in a medium.

The system also includes a flow focusing apparatus. The flow focusing apparatus includes a polymer nozzle and a focusing nozzle. The polymer nozzle operatively delivers a focused stream of the polymer solution and/or suspension. The focusing nozzle operatively delivers a focusing stream of the focusing solution. The flow focusing apparatus operatively delivers the focused stream and the focusing stream into intersection with one another. The flow focusing apparatus operatively flows the focusing stream and the focused stream into the fluid bath, so as to form the microbeads in the fluid bath. The system also includes a liquid-containing cell which is shaped to define an outlet port. The liquid-containing cell operatively contains the fluid bath. The liquid-containing cell operatively delivers a volume of the focusing fluid out from the fluid bath, via the outlet port, so as to concentrate the microbeads in the fluid bath. The liquid-containing cell further includes a stirring bar. The stirring bar operatively maintains the fluid bath under stirring. The fluid bath operatively allows the microbeads to solidify.

According to an aspect of one preferred embodiment of the invention, operative flow rates for (i) the focused stream through the polymer nozzle, (ii) the focusing stream through the focusing nozzle, and/or (iii) the focusing fluid through the outlet port, respectively, may preferably be predetermined—preferably in dependent relation upon one another, and preferably so as to maintain the fluid bath at a substantially constant liquid level.

According to an aspect of one preferred embodiment of the invention, the liquid-containing cell may preferably, but need not necessarily, include one or more filters—preferably, on the outlet port. The volume of the focusing fluid may preferably, but need not necessarily, be operatively delivered, through the filters, preferably out from the fluid bath.

According to an aspect of one preferred embodiment of the invention, the filters may preferably, but need not necessarily, operatively retain the microbeads—preferably, in the fluid bath.

According to an aspect of one preferred embodiment of the invention, the filters may preferably, but need not necessarily, retain a substantially monodisperse set of the microbeads—preferably, in the fluid bath.

According to an aspect of one preferred embodiment of the invention, the filters may preferably, but need not necessarily, operatively divide the microbeads into one or more collections of microbeads. Each of the collections may preferably, but need not necessarily, include a respectively monodisperse set of the microbeads.

According to an aspect of one preferred embodiment of the invention, the flow focusing apparatus may preferably, but need not necessarily, also include a flow focusing body. The flow focusing body may preferably, but need not necessarily, define an interior chamber and an outlet portion. The focused stream and the focusing stream may preferably, but need not necessarily, be operatively delivered into intersection with one another in the chamber. The focusing stream and the focused stream may preferably, but need not necessarily, operatively flow out from the outlet portion of the flow focusing body.

According to an aspect of one preferred embodiment of the invention, the outlet portion of the flow focusing body may preferably, but need not necessarily, be operatively located below a liquid level of the fluid bath.

According to an aspect of one preferred embodiment of the invention, the focused stream may preferably, but need not necessarily, be operatively focused by the focusing fluid. The focusing stream and the focused stream may preferably, but need not necessarily, operatively flow out from the outlet portion as a single flow stream.

According to an aspect of one preferred embodiment of the invention, the focusing stream may preferably, but need not necessarily, substantially surround the focused stream in the single flow stream.

According to an aspect of one preferred embodiment of the invention, the liquid-containing cell may preferably, but need not necessarily, be operatively sealed relative to the outside environment.

According to an aspect of one preferred embodiment of the invention, the flow focusing apparatus may preferably, but need not necessarily, operatively deliver the focused stream and the focusing stream, into intersection with one another, in the liquid-containing cell.

According to an aspect of one preferred embodiment of the invention, the system may preferably, but need not necessarily, also include a volume of a gas—preferably at a predetermined pressure, and preferably operatively contained within the liquid-containing cell.

According to an aspect of one preferred embodiment of the invention, the system may preferably, but need not necessarily, also include a gas pressure source. The liquid-containing cell may preferably, but need not necessarily, be shaped to define an inlet valve. The gas pressure source may preferably, but need not necessarily, operatively pressurize the gas—preferably via the inlet valve, and preferably in the liquid-containing cell.

According to an aspect of one preferred embodiment of the invention, the liquid-containing cell may preferably, but need not necessarily, be shaped to define a pressure safety valve. The pressure safety valve may preferably, but need not necessarily, operatively release a portion of the gas and/or the fluid bath—preferably, when the pressure exceeds a predetermined maximum safety pressure for the sealed liquid-containing cell.

According to an aspect of one preferred embodiment of the invention, the pressure safety valve may preferably, but need not necessarily, be provided on, and/or in operative fluid relation with, the outlet port of the liquid-containing cell. The pressure safety valve may preferably, but need not necessarily, operatively release a portion of the fluid bath, preferably when the pressure exceeds the predetermined maximum safety pressure.

According to an aspect of one preferred embodiment of the invention, the gas may preferably, but need not necessarily, include an inert gas.

According to an aspect of one preferred embodiment of the invention, (i) the pressure of the gas, and/or operative flow rates for (ii) the focused stream through the polymer nozzle and/or (iii) the focusing stream through the focusing nozzle, may preferably be predetermined—preferably in dependent relation upon one another, and preferably so as to maintain the fluid bath at a substantially constant liquid level.

According to an aspect of one preferred embodiment of the invention, the stirring bar may preferably, but need not necessarily, include an electric stirring bar and/or a magnetic stirring bar.

According to an aspect of one preferred embodiment of the invention, the liquid-containing cell may preferably, but need not necessarily, be shaped to define a sealed orifice. The sealed orifice may preferably, but need not necessarily, be selectively openable—preferably so as to recover substantially solidified microbeads through the orifice, from the fluid bath.

According to an aspect of one preferred embodiment of the invention, the system may preferably, but need not necessarily, also include a conduit in fluid communication between the outlet port and the focusing nozzle—preferably, so as to operatively recycle at least part of the volume of the focusing fluid operatively delivered out from the fluid bath, preferably via the outlet port, and preferably as at least part of the focusing stream operatively delivered by the focusing nozzle.

According to the invention, there is additionally disclosed a further system for forming one or more concentrated volumes of microbeads. The system includes a fluid bath, a focusing fluid, and a polymer solution and/or suspension including a polymer dissolved and/or dispersed in a medium. The system also includes a flow focusing apparatus. The flow focusing apparatus includes a polymer nozzle and a focusing nozzle. The polymer nozzle operatively delivers a focused stream of the polymer solution and/or suspension. The focusing nozzle operatively delivers a focusing stream of the focusing solution. The flow focusing apparatus operatively delivers the focused stream and the focusing stream into intersection with one another. The flow focusing apparatus operatively flows the focusing stream and the focused stream into the fluid bath, so as to form the microbeads in the fluid bath. The system also includes a liquid-containing cell which is shaped to define an outlet port. The liquid-containing cell operatively contains the fluid bath. The liquid-containing cell operatively delivers a volume of the focusing fluid out from the fluid bath, via the outlet port, so as to concentrate the microbeads in the fluid bath. The system also includes a conduit in fluid communication between the outlet port and the focusing nozzle—so as to operatively recycle at least part of the volume of the focusing fluid operatively delivered out from the fluid bath, via the outlet port, as at least part of the focusing stream operatively delivered by the focusing nozzle.

According to an aspect of one preferred embodiment of the invention, the medium may preferably, but need not necessarily, include an organic solvent.

According to an aspect of one preferred embodiment of the invention, the organic solvent may preferably, but need not necessarily, include chloroform and/or dichloromethane.

According to an aspect of one preferred embodiment of the invention, the polymer may preferably, but need not necessarily, be substantially hydrophobic.

According to an aspect of one preferred embodiment of the invention, the polymer may preferably, but need not necessarily, include a polystyrene powder and/or a derivative thereof.

According to an aspect of one preferred embodiment of the invention, the focusing fluid may preferably, but need not necessarily, include water.

According to an aspect of one preferred embodiment of the invention, the polymer solution and/or suspension may preferably, but need not necessarily, also include particles dissolved and/or dispersed in the medium. Each of the microbeads may preferably, but need not necessarily, bind an identifiable set of the particles.

According to an aspect of one preferred embodiment of the invention, the particles may preferably, but need not necessarily, include fluorophores.

According to an aspect of one preferred embodiment of the invention, the particles may preferably, but need not necessarily, include nanoparticles.

According to an aspect of one preferred embodiment of the invention, the nanoparticles may preferably, but need not necessarily, include semiconductor nanoparticles, magnetic nanoparticles, metallic conductor nanoparticles, metal oxide nanoparticles, and/or fluorescent nanoparticles.

According to an aspect of one preferred embodiment of the invention, the particles may preferably, but need not necessarily, include quantum dots.

According to an aspect of one preferred embodiment of the invention, the particles may preferably, but need not necessarily, include a combination of quantum dots and/or magnetic nanoparticles.

According to an aspect of one preferred embodiment of the invention, the polymer solution and/or suspension may preferably, but need not necessarily, have a concentration of about 0.04 by weight-weight percentage (4 wt %).

According to the invention, there is disclosed still another system for forming one or more concentrated volumes of microbeads. The system is for use with a fluid bath, a focusing fluid, and/or a polymer solution and/or suspension. The polymer solution and/or suspension includes a polymer dissolved and/or dispersed in a medium. The system includes a flow focusing apparatus. The flow focusing apparatus includes a polymer nozzle and a focusing nozzle. The polymer nozzle operatively delivers a focused stream of the polymer solution and/or suspension. The focusing nozzle operatively delivers a focusing stream of the focusing solution. The flow focusing apparatus operatively delivers the focused stream and the focusing stream into intersection with one another. The flow focusing apparatus operatively flows the focusing stream and the focused stream into the fluid bath, so as to form the microbeads in the fluid bath. The system also includes a liquid-containing cell which is shaped to define an outlet port. The liquid-containing cell operatively contains the fluid bath and operatively delivers a volume of the focusing fluid out from the fluid bath, via the outlet port, so as to concentrate the microbeads in the fluid bath.

According to the invention, there is disclosed a further system for forming one or more concentrated volumes of microbeads. The system is for use with a fluid bath, a focusing fluid, and/or a polymer solution and/or suspension. The polymer solution and/or suspension includes a polymer dissolved and/or dispersed in a medium. The system includes a flow focusing apparatus. The flow focusing apparatus includes a polymer nozzle and a focusing nozzle. The polymer nozzle operatively delivers a focused stream of the polymer solution and/or suspension. The focusing nozzle operatively delivers a focusing stream of the focusing solution. The flow focusing apparatus operatively delivers the focused stream and the focusing stream into intersection with one another. The flow focusing apparatus operatively flows the focusing stream and the focused stream into the fluid bath, so as to form the microbeads in the fluid bath. The system also includes a liquid-containing cell which is shaped to define an outlet port. The liquid-containing cell operatively contains the fluid bath and operatively delivers a volume of the focusing fluid out from the fluid bath, via the outlet port, so as to concentrate the microbeads in the fluid bath. The liquid-containing cell further includes a stirring bar. The stirring bar operatively maintains the fluid bath under stirring. The fluid bath operatively allows the microbeads to solidify.

According to the invention, there is disclosed yet another system for forming one or more concentrated volumes of microbeads. The system is for use with a fluid bath, a focusing fluid, and/or a polymer solution and/or suspension. The polymer solution and/or suspension includes a polymer dissolved and/or dispersed in a medium. The system includes a flow focusing apparatus. The flow focusing apparatus includes a polymer nozzle and a focusing nozzle. The polymer nozzle operatively delivers a focused stream of the polymer solution and/or suspension. The focusing nozzle operatively delivers a focusing stream of the focusing solution. The flow focusing apparatus operatively delivers the focused stream and the focusing stream into intersection with one another. The flow focusing apparatus operatively flows the focusing stream and the focused stream into the fluid bath, so as to form the microbeads in the fluid bath. The system also includes a liquid-containing cell which is shaped to define an outlet port. The liquid-containing cell operatively contains the fluid bath and operatively delivers a volume of the focusing fluid out from the fluid bath, via the outlet port, so as to concentrate the microbeads in the fluid bath. The system also includes a conduit in fluid communication between the outlet port and the focusing nozzle—so as to operatively recycle at least part of the volume of the focusing fluid operatively delivered out from the fluid bath, via the outlet port, as at least part of the focusing stream operatively delivered by the focusing nozzle.

To put it another way, the invention may be said to include a method of manufacturing polymer microspheres. This inventive method includes the steps of: (a) directing a focusing fluid through a focusing nozzle to create a focusing stream; (b) directing a polymer solution and/or suspension (or "focused fluid") through a polymer nozzle to create a focused stream; (c) intersecting the focusing stream and the focused stream inside a liquid-containing cell—preferably, but not necessarily, below the liquid level in the cell—to form the microspheres. The concentration of the microspheres in the cell may preferably, but need not necessarily, be controlled by adjusting a volume of liquid in the cell.

According to an aspect of one preferred embodiment of the invention, the focused fluid may preferably, but need not necessarily, include a polymer solution and/or suspension. The focusing fluid may preferably, but need not necessarily, include water.

According to an aspect of one preferred embodiment, the invention also extends to a system for manufacturing polymer microspheres. The system includes a liquid-containing cell and a nozzle assembly. The nozzle assembly may preferably be positioned within the cell. The nozzle assembly may preferably include a focusing nozzle producing the focusing stream and a polymer nozzle (or "focused nozzle") producing a stream of the focused fluid. The nozzles are preferably operative to intersect the focusing stream with the stream of the focused fluid, so as to form microspheres from the focused fluid.

Other advantages, features and/or characteristics of the present invention, as well as methods of operation and/or functions of the related elements of the method and system, and/or the combination of steps, parts and/or economies of manufacture, will become more apparent upon consideration of the following detailed description and the appended claims with reference to the accompanying drawings, the latter of which are briefly described hereinbelow.

BRIEF DESCRIPTION OF THE DRAWINGS

The novel features which are believed to be characteristic of the system and method according to the present invention, as to their structure, organization, use, and method of operation, together with further objectives and advantages thereof, will be better understood from the following drawings in which presently preferred embodiments of the invention will now be illustrated by way of example. It is expressly understood, however, that the drawings are for the purpose of illustration and description only, and are not intended as a definition of the limits of the invention. In the accompanying drawings.

DETAILED DESCRIPTION OF THE PREFERRED EMBODIMENTS

Referring now to FIGS. 1-4, it will be appreciated that the inventive system and method presented herein may preferably include, or be used in conjunction with, a fluid bath 306, a focusing fluid 300, and a focused fluid (preferably, a polymer solution and/or suspension) 150.

Figure 1:
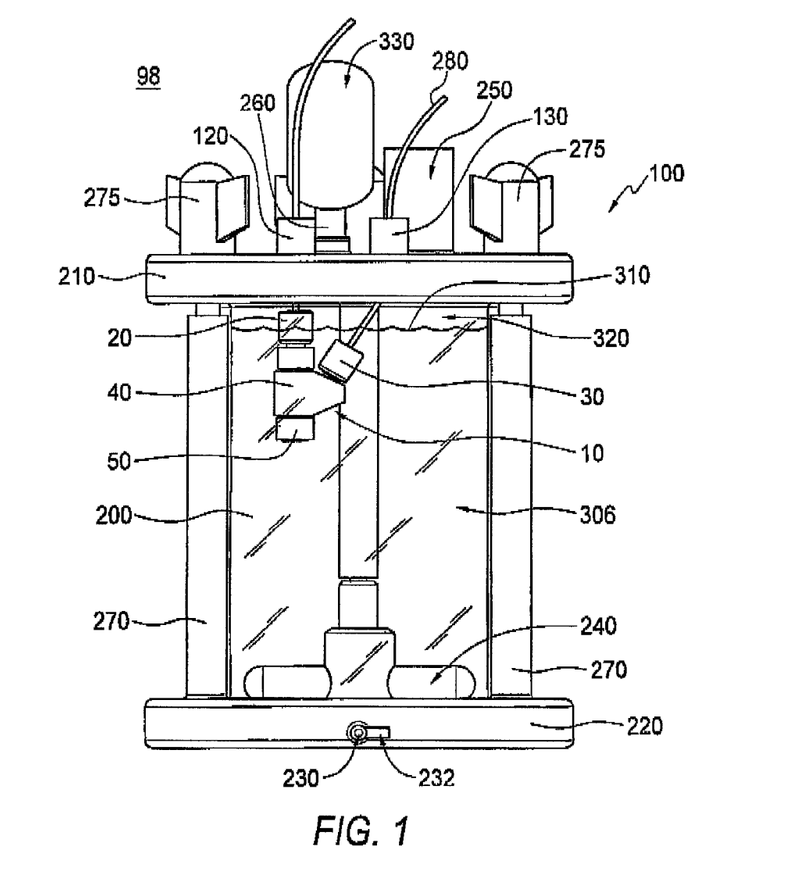
FIG. 1 is a front view of a system for forming a concentrated volume of microbeads according to a preferred embodiment of the present invention.

As shown in FIG. 1, the system preferably includes a flow focusing apparatus 10 and a liquid-containing cell 100. The flow focusing apparatus 10 includes two fluid nozzles—i.e., a focused fluid nozzle (alternately referred to as a "polymer nozzle") 20 and a focusing nozzle 30. Preferably, the polymer solution and/or suspension 150 is fed to the polymer nozzle 20. The focusing fluid 300 is fed to the focusing nozzle 30. The flow focusing apparatus 10 also includes a flow focusing body 40 which has an interior chamber 46—operatively, a locus for an intersection 154 of a focused stream 152 flowing from the polymer nozzle 20 and a focusing stream 302 flowing from the focusing nozzle 30.

The focusing fluid 300 in the focusing stream 302 is directed into contact with the focused stream (alternately, referred to as the "polymer stream") 152 in the interior chamber 46 of the focusing body 40, so as to focus the polymer stream 152 toward an outlet portion 50 of the flow focusing body 40.

Figure 3:
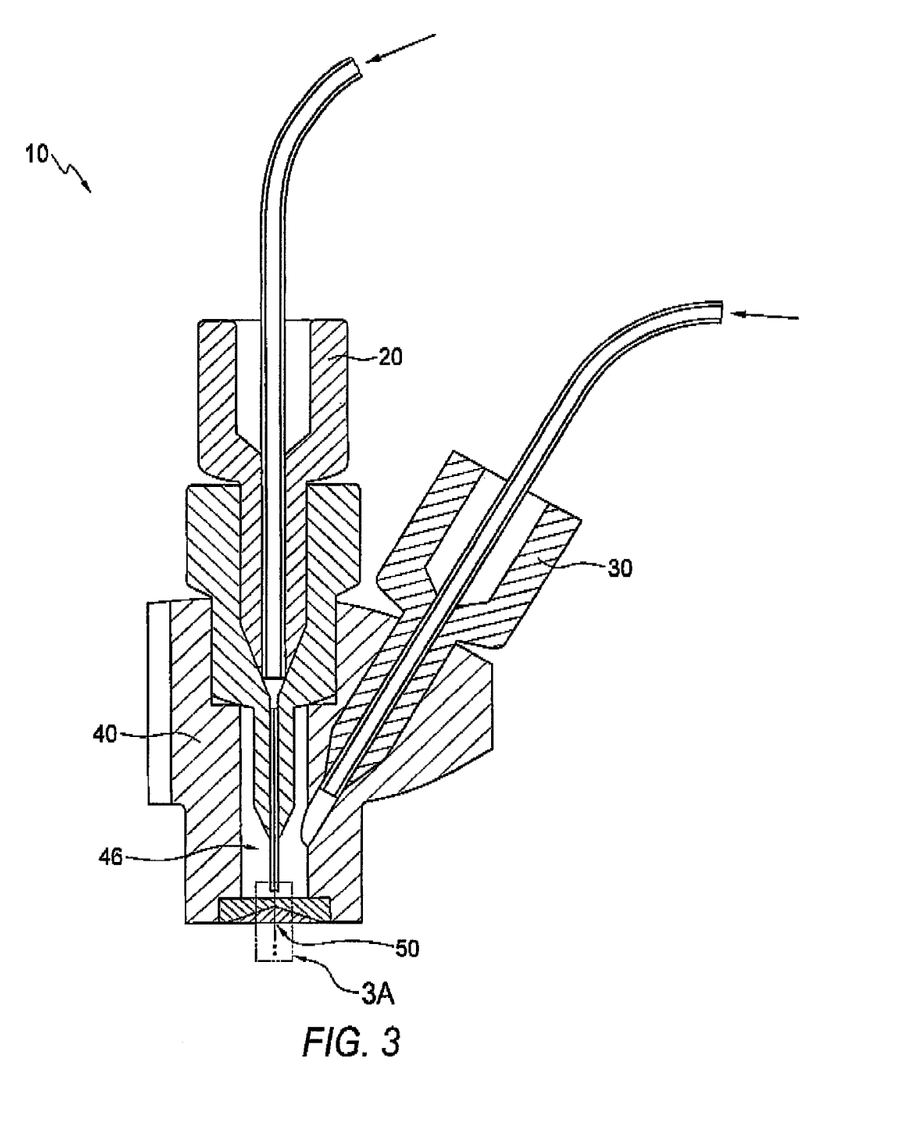
FIG. 3 is a sectional front view of a flow focusing apparatus of the system of FIG. 1, showing area 3A in phantom outline.
Figure 3A:
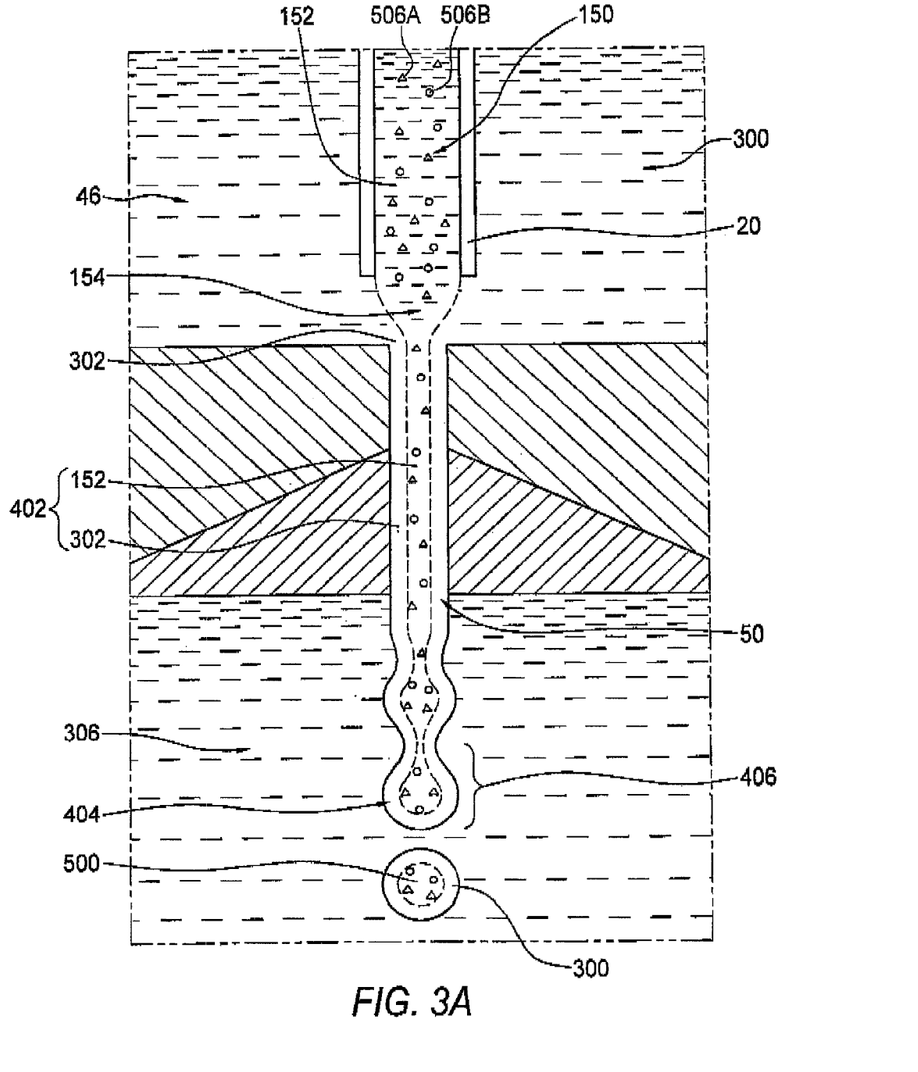
FIG. 3A is an enlarged view of area 3A from FIG. 3.

From the intersection 154 (and as best seen in FIG. 3A), the focused stream 152 and the focusing stream 302 flow as a single flow stream 402, through the outlet portion (or "pinhole") 50, and out of the flow focusing body 40. The focusing fluid 300 (in the focusing stream 302) and the polymer stream 152 focused thereby flow, as the single flow stream 402, out from the interior chamber 46 and through the pinhole 50. At that point, the focusing stream 302 substantially surrounds the focused stream 152 in the single flow stream 402. The single flow stream 402 then flows out from the outlet portion 50 of the focusing body 40.

Pendant droplets 406 detach from a leading edge portion 404 of the single flow stream 402, so as to form microbeads 500 (still wet) which are surrounded by the focusing liquid 300 in the fluid bath 306.

One preferred embodiment of the present invention utilizes a polystyrene polymer solution and/or suspension as the focused fluid 150, and water as the focusing fluid 300. This preferred embodiment is suitable to create polystyrene microbeads 500.

The microbeads 500 are collected within the fluid bath 306 inside the liquid-containing cell 100. Subsequently, the microbeads 500 are solidified.

In a preferred embodiment according to the present invention, and as best seen in FIG. 1, the outlet portion 50 of the flow focusing body 40 is immersed in the fluid bath 306. Preferably, the fluid bath 306 also contains the focusing fluid 300—i.e., preferably, a water solution. The fluid bath 306 may preferably be maintained under stirring conditions (as described elsewhere herein) for the duration of the process of solidifying the microbeads 500. The microbeads 500 are preferably allowed to solidify before being recovered from the fluid bath 306.

The flow focusing apparatus 10 is incorporated into the liquid-containing cell 100, as shown in FIG. 1. The ends of the nozzles 20, 30 are within the cell 100. As such, the fluid streams 152, 302, 402 are emitted within the volume of the cell 100. The cell 100 is shown in more detail in FIG. 2.

Figure 2:
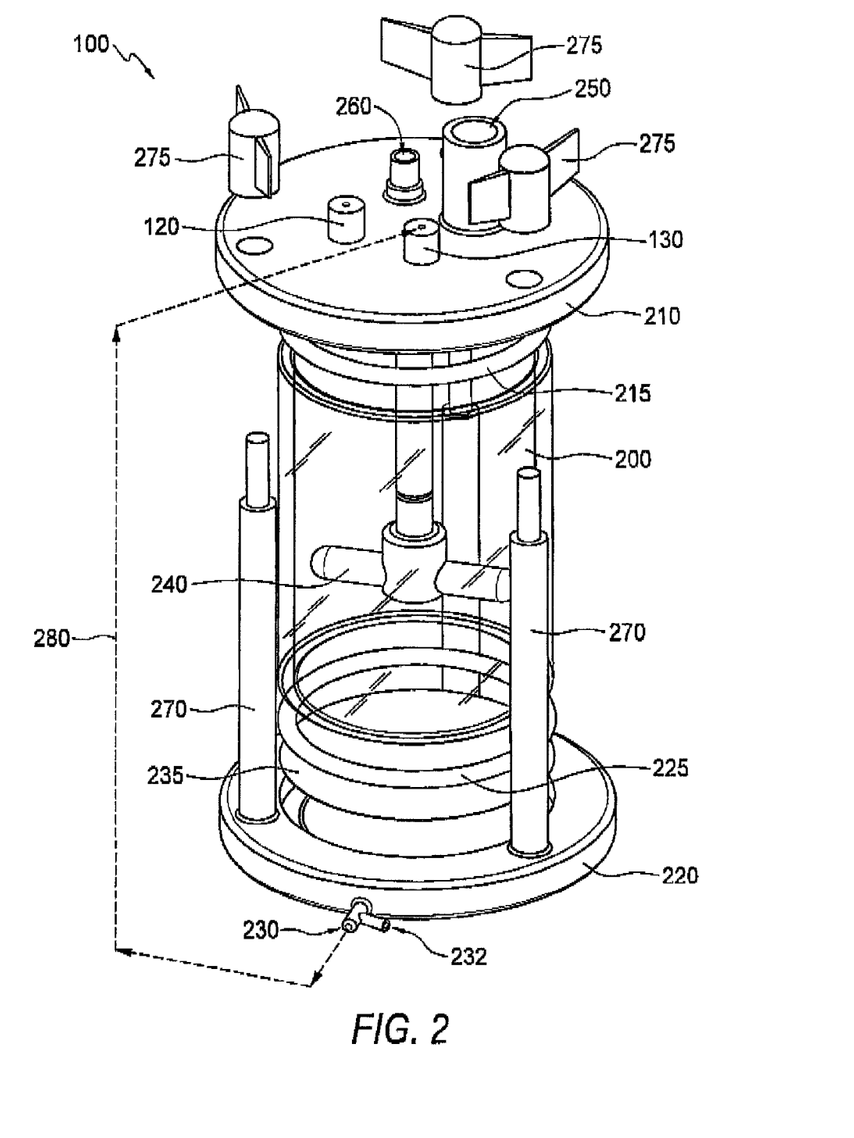
FIG. 2 is an exploded view of the system shown in FIG. 1.

The cell 100 includes a glass cylinder 200 sealed to an upper plate 210 and a lower plate 220 by o-rings 215 and 225, respectively. Although atmospheric pressure may preferably be sufficient to push the filtrate through a filter 235 and into filtrate port 230, additional pressure may be provided via a pressure inlet valve 260. As best seen in FIG. 1, the cell 100 may preferably be operatively sealed relative to the outside environment 98. The cell 100 may be pressurized via a gas pressure source 330 supplying a pressurized, preferably inert, gas 320 (e.g., nitrogen) through pressure inlet valve 260.

A pressure safety valve 232 may preferably be mounted on the filtrate port 230 (alternately, referred to as the outlet port 230), so as to help control the pressure within the cell 100, and so as to obviate (or reduce) any risk that the cell 100 might otherwise exceed a maximum pressure which the glass cylinder 200 is able to sustain. For some exemplary glass cylinders 200, the maximum pressure may typically be about 6 bar (90 psi).

Fluid inlet ports 120, 130 preferably supply the polymer solution and/or suspension 150 and the focusing fluid 300, respectively, into the cell 100 and to the nozzles 20, 30 as shown in FIG. 1. A first one of the fluid inlet ports 120 supplies the polymer solution and/or suspension 150 to the polymer nozzle 20, and a second one of the fluid inlet ports 130 supplies the focusing fluid 300 to the focusing nozzle 30.

A selectively openable orifice 250 allows the introduction of water into the fluid bath 306 in the cell 100. The flow focusing apparatus 10 is preferably immersed in the fluid bath 306. At the end of the process, suspended and solidified microbeads 500 may preferably be removed from the cell 100 through the orifice 250.

A stirring bar 240, either magnetic or electric, is preferably provided to stir the contents of the cell 100 for the duration of the process of solidifying the microbeads 500.

As best seen in FIG. 2, the cell 100 may be selectively assembled and/or disassembled by means of support posts 270 and screw knobs 275. Other assembly and disassembly methods previously known in the art may, however, be used in place thereof.

The size of the microbeads 500 formed according to the present invention may be dependent upon the flow rates in the nozzles 20, 30 and the concentration of the polymer used. The microbeads 500 are preferably retained (or trapped) within the cell 100 by the filter 235. A volume of the focusing fluid 300 (preferably, water) is preferably removed from the fluid bath 306, via the filtrate port 230. The filter type may be predetermined in dependent relation upon on the size of the microbeads 500 which are sought to be accumulated in the fluid bath 306.

The filter 235 may also be used to ensure, facilitate or increase the likelihood of monodispersity of the microbeads 500. (Though not shown in the drawings, it is contemplated that a series of increasingly fine filters 235 might be used to divide the microbeads 500 into a plurality of collections of differing monodispersity.) In these and other contemplated embodiments, there may exist some risk of one or more filters 235 becoming clogged, and/or of further purification of the focusing fluid 300 being required (e.g., before recycling the focusing fluid 300).

EXAMPLE 1

To generate 6 μm polystyrene beads using the method and system described herein, a commercial polystyrene powder (offered by Sigma-Aldrich Canada Ltd. of Oakville, Ontario, Canada) was dissolved and/or dispersed into dichloromethane to create a 4% polymer solution and/or suspension. The resulting solution was then introduced into a commercial nozzle (i.e., an Avant-1™ nozzle offered by Ingeniatrics S.L. of Seville, Spain) using a syringe pump (i.e., a SP100I™ syringe pump offered by World Precision Instruments, Inc. of Sarasota, Fla., U.S.A.) at a rate of 1 mL/h, along with water as the focusing fluid 300, using a digital gear pump (offered by the Cole-Parmer Instrument Company of Vernon Hills, Ill., U.S.A.) at a rate of 180 mL/h. During the reaction, the nozzle inside the ultrafiltration cell was immersed into a 100 mL water solution under stirring. The volume of water solution used is dependent on the volume of the cell 100 and the location of the nozzle. Mixed cellulose ester filters 235 of 0.65 μm size (offered by the Millipore Corporation of Billerica, Mass., U.S.A.) were used. After synthesis, the filtrate port 230 was closed and suspended microbeads 500 were removed through the orifice 250.

EXAMPLE 2

To create 5 μm polystyrene beads using the method and system described herein, a commercial polystyrene powder (offered by Sigma-Aldrich Canada Ltd. of Oakville, Ontario, Canada) was dissolved and/or dispersed into dichloromethane to create a 4% polymer solution and/or suspension. The resulting solution was then introduced into a commercial nozzle (i.e., an Avant-1™ nozzle offered by Ingeniatrics S.L. of Seville, Spain) using a syringe pump (i.e., a SP100I™ syringe pump offered by World Precision Instruments, Inc. of Sarasota, Fla., U.S.A.) at a rate of 0.5 mL/h, along with water as the focusing fluid 300, using a digital gear pump (offered by the Cole-Parmer Instrument Company of Vernon Hills, Ill., U.S.A.) at a rate of 180 mL/h During the reaction, the nozzle inside the ultrafiltration cell was immersed into a 100 mL water solution under stirring. The volume of water solution used is dependent on the volume of the cell 100 and the location of the nozzle. Mixed cellulose ester filters 235 of 0.65 μm size (offered by the Millipore Corporation of Billerica, Mass., U.S.A.) were used. After synthesis, the filtrate port 230 is closed and suspended microbeads 500 are removed through the orifice 250.

By controlling a liquid level 310 within the cell 100 in accordance with the flow rates of the focused solution 150 and the focusing fluid 300, an equilibrium point may preferably be achieved. In this manner, and due in part to atmospheric pressure, the volume of the liquid suspension of the microbeads 500 in the cell 100 stays substantially constant over time. Excess focusing fluid 300 is filtered out. As such, the concentration of the microbeads 500 within the cell 100 increases. Accordingly, a higher concentration of the microbeads 500 may preferably be produced in a smaller volume of the fluid bath 306, preferably without the need for multiple centrifugations and/or for other concentration steps. Additionally, the extracted liquid can be recycled and fed back in as the focusing fluid 300, via a conduit 280 (best seen in FIGS. 1 and 2). In this way, the system and method according to the present invention may preferably help to reduce the need for large volumes of the focusing fluid 300 in large-scale production of microbeads 500.

For example, use of the present concentration-controlled flow focusing method and system to synthesize 5 μm microbeads over a period of 10 hours—using a 300 mL cell with the volume of the microbead suspension within the cell being kept at 100 mL—would produce about 5820 million microbeads at a concentration of about 0.4 wt %. The 100 mL suspension of microbeads may be further concentrated by splitting the volume into 2×50 mL Falcon tubes and centrifuging them. By contrast, over the same 10 hour period, prior art synthesis methods might produce roughly the same number of microbeads (i.e., about 5820 million microbeads), but at a concentration of only 0.02 wt % in a total volume of 1.9 L (1910 mL). To then concentrate this solution would require the use of 39×50 ml Falcon tubes. In this example, the present invention provides a microbead solution that is about 20 times more concentrated, over the same 10 hour period. Use of a smaller cell may be expected to yield even more concentrated bead solutions, perhaps up to 200 times that of the previous synthesis methods.

Figure 4:
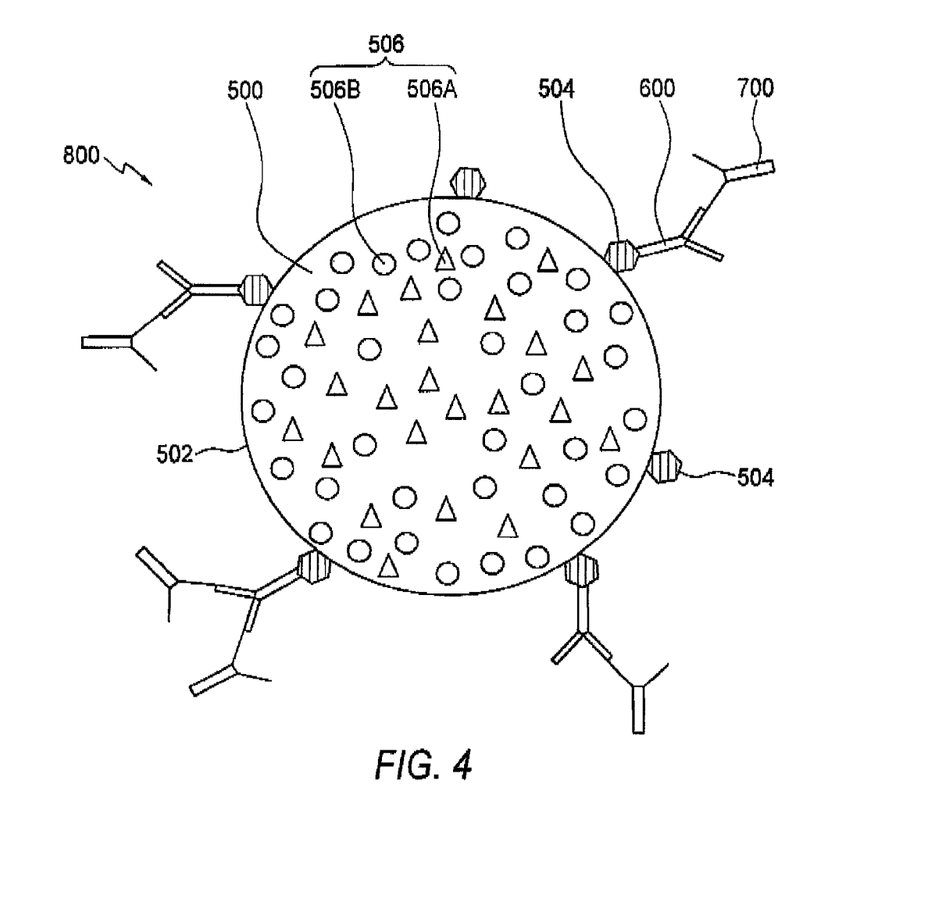
FIG. 4 is an illustrative representation of a conjugated and bound microbead according to a preferred embodiment of the present invention.

Referring now to FIG. 4, there is depicted a conjugate 800 including a microbead 500 produced according to a preferred embodiment of the present invention. The microbead 500 contains a set of particles 506—more particularly, a set 506 of two types of quantum dots 506A, 506B—encapsulated within the microbead 500. A surface 502 of the microbead 500 possesses functional groups 504 operatively bound with the biorecognition molecules 600 that are themselves operatively bound to target molecules 700 (e.g., markers for infections, diseases and/or genetic expression factors).

The identifiable set 506 of the quantum dots 506A, 506B may be adapted to, following irradiation, produce one or more identifiable spectral signals based on color and/or intensity.

Other modifications and alterations may be used in the design and manufacture of other embodiments according to the present invention without departing from the spirit and scope of the invention, which, is limited only by the accompanying claims of this application.

While the above preferred embodiments have been presented in the context of QDs, the method and system is equally applicable to other particle, including nanoparticles. Types of nanoparticles which are capable of being used in conjunction with the method and system according to the present invention may preferably include, but are not limited to, hard nanoparticles, polymer nanoparticles, magnetic nanoparticles, metallic conductor nanoparticles, metal oxide nanoparticles, fluorescent nanoparticles, and phosphorescent nanoparticles.

The foregoing description has been presented for the purpose of illustration and is not intended to be exhaustive or to limit the invention to the precise form disclosed. Many modifications and variations are possible in light of the above teaching and will be apparent to those skilled in the art. It is intended the scope of the invention be limited not by this description but by the claims.

What is claimed is:

1. A method of forming one or more concentrated volumes of microbeads, the method comprising the steps of:
   (a) flowing, a focused stream of a polymer solution, polymer suspension, or polymer solution and suspension towards a fluid bath, with the polymer solution, polymer suspension, or polymer solution and suspension comprising a polymer dissolved, dispersed, or dissolved and dispersed in a medium;
   (b) flowing a focusing stream of a focusing fluid towards the fluid bath, and into intersection with the focused stream;
   (b.1) after step (b), maintaining the fluid bath under stirring so that the focusing fluid and the polymer solution continue to be mixed and intermingled;
   (c) after step (b), flowing the focusing stream and the focused stream into the fluid bath and allowing the microbeads to, thus, form and solidify in the fluid bath;
   (d) flowing a volume of the focusing fluid from the fluid bath while leaving the microbeads in the fluid bath, so as to concentrate the microbeads in the fluid bath; and
   (e) recycling at least part of the volume of the focusing fluid, flowing from the fluid bath in step (d), as at least part of the focusing stream flowing into intersection with the focused stream in step (b).

2. The method according to claim 1, wherein in step (d), the fluid bath is controlled so as to be maintained at a substantially constant liquid level.

3. The method according to claim 2, wherein the substantially constant liquid level is maintained by balancing respective flow rates for the focused stream in step (a), the focusing stream in step (b), and the focusing fluid in step (d).

4. The method according to claim 1, wherein in step (d), the volume of the focusing fluid flows through one or more filters.

5. The method according to claim 4, wherein in step (d), the filters retain the microbeads in the fluid bath.

6. The method according to claim 4, wherein in step (d), the filters retain a substantially monodisperse set of the microbeads in the fluid bath.

7. The method according to claim 4, wherein in step (d), the filters divide the microbeads into one or more collections of microbeads, with each of the collections including a respectively monodisperse set of the microbeads.

8. The method according to claim 1, wherein at least one of steps (a) and (b) is performed within an interior chamber of a flow focusing body.

9. The method according to claim 8, wherein steps (a) and (b) are both performed within the interior chamber of the flow focusing body, with an outlet portion of the flow focusing body being located below a liquid level of the fluid bath, and wherein in step (c), the focusing stream and the focused stream flow out from the outlet portion of the flow focusing body.

10. The method according to claim 9, wherein in step (b), the focused stream is focused by the focusing fluid, and wherein in step (c), the focusing stream and the focused stream flow out from the outlet portion as a single flow stream.

11. The method according to claim 10, wherein in step (c), the focusing stream substantially surrounds the focused stream in the single flow stream.

12. The method according to claim 1, further comprising a preliminary step, before step (a), of providing the fluid bath within a sealed liquid-containing cell.

13. The method according to claim 12, wherein at least one of steps (a) through (c) is performed within the liquid-containing cell.

14. The method according to claim 12, wherein in the preliminary step, the liquid-containing cell additionally contains a volume of a gas at a predetermined pressure.

15. The method according to claim 14, wherein in the preliminary step, a gas pressure source pressurizes the gas, via an inlet valve, in the sealed liquid-containing cell.

16. The method according to claim 14, further comprising step (c.1), after the preliminary step, of releasing a portion of the gas or the fluid bath, via a pressure safety valve, when the pressure exceeds a predetermined maximum safety pressure for the sealed liquid-containing cell.

17. The method according to claim 14, wherein the gas comprises an inert gas.

18. The method according to claim 14, wherein the pressure of the gas in the preliminary step is predetermined, in balance with respect to respective flow rates for the focused stream in step (a) and the focusing stream in step (b), to maintain the fluid bath at a substantially constant liquid level.

19. The method according to claim 1, wherein in step (b.1), a stirring bar maintains the fluid bath under stirring, and wherein the stirring bar comprises an electric stirring bar or a magnetic stirring bar.

20. The method according to claim 1, further comprising step (d.1), after step (d), of recovering solidified microbeads from the fluid bath.

21. The method according to claim 1, wherein in step (a), the medium comprises an organic solvent.

22. The method according to claim 21, wherein the organic solvent comprises chloroform or dichloromethane.

23. The method according to claim 1, wherein in step (a), the polymer is substantially hydrophobic.

24. The method according to claim 1, wherein in step (a), the polymer comprises a polystyrene powder or a derivative thereof.

25. The method according to claim 1, wherein in step (b), the focusing fluid comprises water.

26. The method according to claim 1, wherein in step (a), the polymer solution further comprises particles dissolved, dispersed, or dissolved and dispersed in the medium, and wherein in step (c), each of the microbeads binds an identifiable set of the particles.

27. The method according to claim 26, wherein in step (a), the particles comprise fluorophores.

28. The method according to claim 26, wherein in step (a), the particles comprise nanoparticles.

29. The method according to claim 28, wherein the nanoparticles comprise semiconductor nanoparticles, magnetic nanoparticles, metallic conductor nanoparticles, metal oxide nanoparticles, fluorescent nanoparticles, or phosphorescent nanoparticles.

30. The method according to claim 26, wherein in step (a), the particles comprise quantum dots.

31. The method according to claim 26, wherein in step (a), the particles comprise a combination of quantum dots and magnetic nanoparticles.

32. The method according to claim 1, wherein in step (a), the polymer solution, polymer suspension, or polymer solution and suspension has a concentration of about 0.04 by weight-weight percentage (4 wt %).

* * * * *

UNITED STATES PATENT AND TRADEMARK OFFICE
CERTIFICATE OF CORRECTION

PATENT NO. : 8,551,763 B2
APPLICATION NO. : 12/682710
DATED : October 8, 2013
INVENTOR(S) : Fournier-Bidoz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 289 days.

Signed and Sealed this

Fifteenth Day of September, 2015

Michelle K. Lee
*Director of the United States Patent and Trademark Office*